United States Patent [19]

Arbuckle

[11] 4,235,177
[45] Nov. 25, 1980

[54] SUTURING DEVICE

[75] Inventor: Norman B. Arbuckle, Costa Mesa, Calif.

[73] Assignee: Raymond C. Kelder, Rancho Mirage, Calif. ; a part interest

[21] Appl. No.: 14,706

[22] Filed: Feb. 23, 1979

[51] Int. Cl.³ .............................................. D05B 1/00
[52] U.S. Cl. .................................. 112/169; 128/334 R
[58] Field of Search ............. 112/169, 80; 128/334 R, 128/334 C, 335, 339

[56] References Cited

U.S. PATENT DOCUMENTS

| | | | |
|---|---|---|---|
| 2,945,460 | 7/1960 | Kagiyama | 112/169 |
| 4,123,982 | 11/1978 | Bess, Jr. et al. | 112/169 |

FOREIGN PATENT DOCUMENTS

| | | | |
|---|---|---|---|
| 1239654 | 5/1967 | Fed. Rep. of Germany | 112/169 |
| 651455 | 2/1929 | France | 112/169 |
| 501317 | 11/1954 | Italy | 112/169 |

Primary Examiner—Werner H. Schroeder
Assistant Examiner—Andrew M. Falik
Attorney, Agent, or Firm—Gordon L. Peterson

[57] ABSTRACT

A suturing device comprising a drive shaft and an oscillator for oscillating the drive shaft about an oscillatory axis. A suturing needle is coupled to the drive shaft so that the drive shaft can move the suturing needle back and forth along a first path. A loop arm is mounted for movement along a second path generally transverse to the oscillatory axis. The loop arm is drivingly coupled to the drive shaft to permit the drive shaft to move the loop arm back and forth along the second path.

11 Claims, 11 Drawing Figures

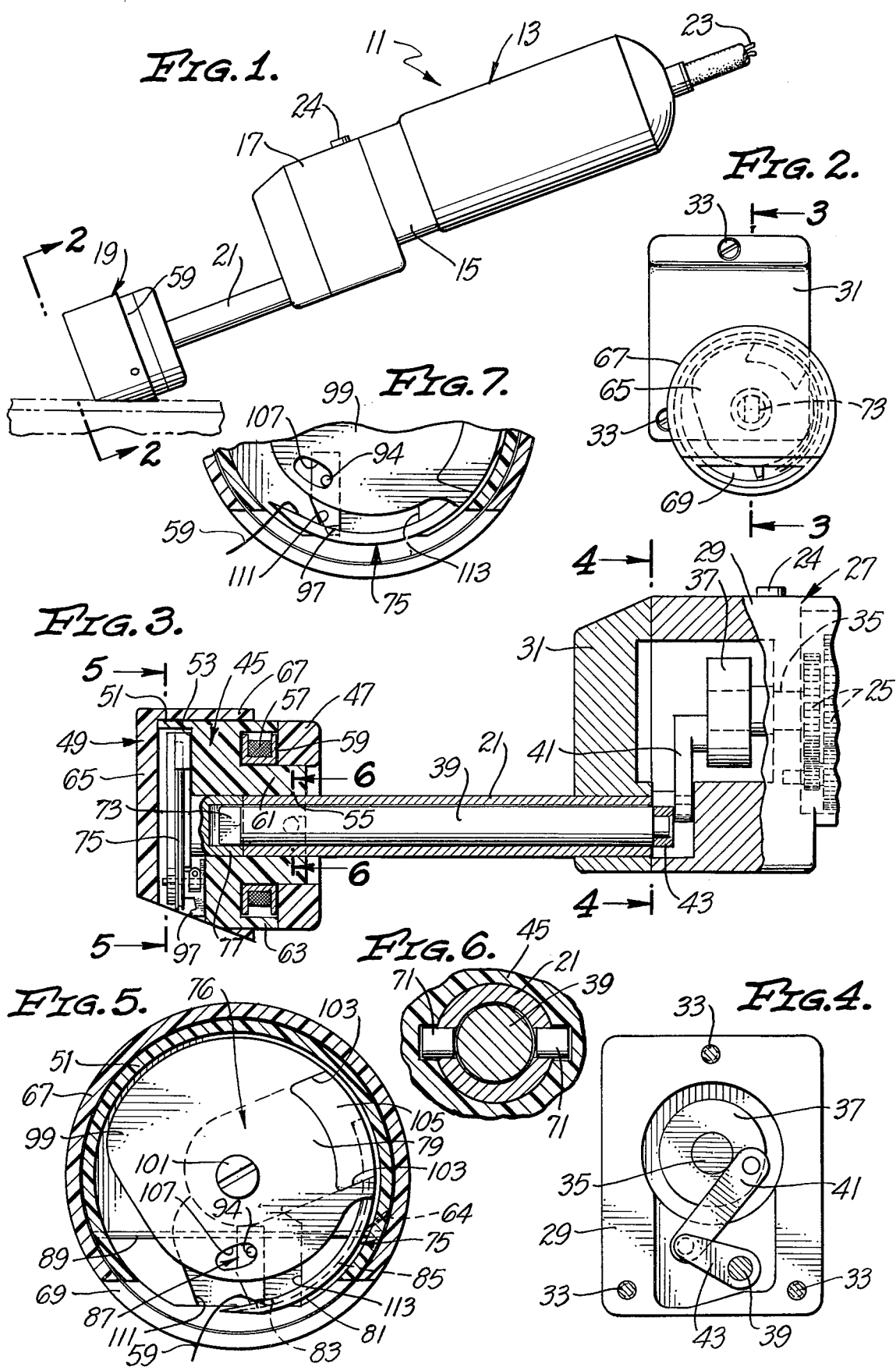

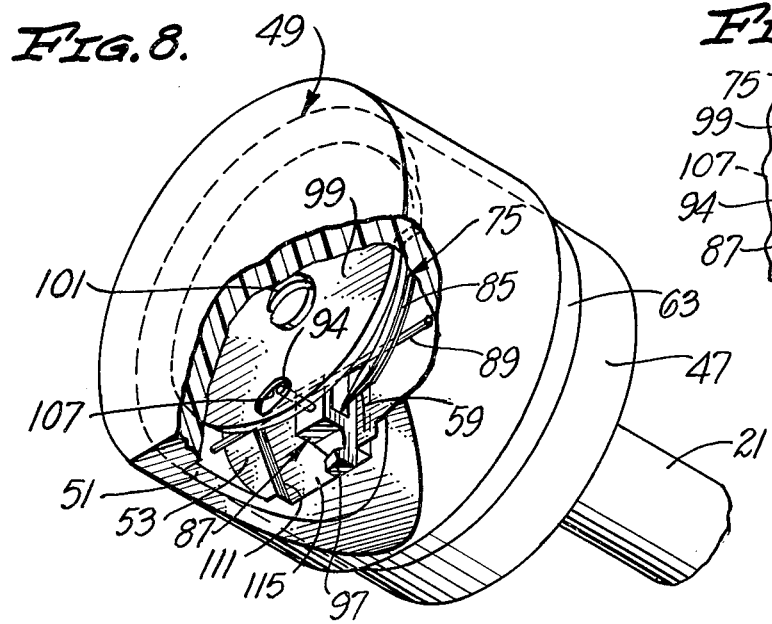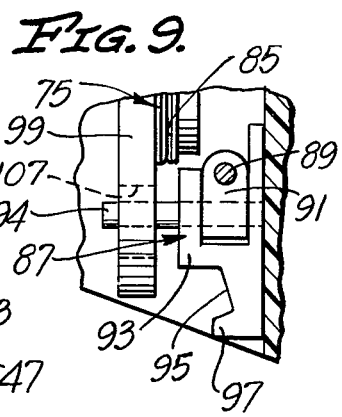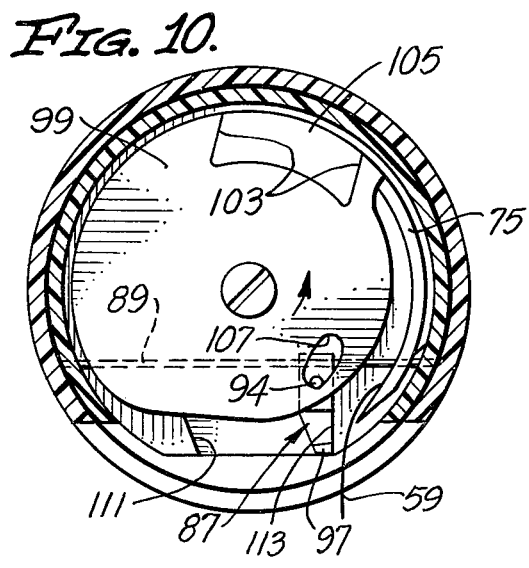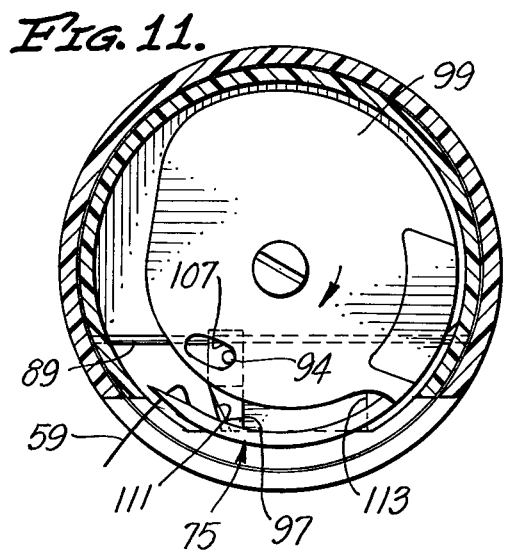

SUTURING DEVICE

BACKGROUND OF THE INVENTION

Suturing of incisions in humans, animals and cadavers is often performed by hand. However, hand suturing is time consuming, can result in uneven stitches and can spread disease if the person performing the suturing is pricked with the suturing needle. Drawbacks, such as these, to hand suturing have led to the development of motorized suturing devices, such as those described in the following U.S. patents:

Alcamo U.S. Pat. No. 2,988,028;
Arbuckle U.S. Pat. No. 4,027,608; and
Bess et al U.S. Pat. No. 4,123,982.

A primary problem with prior art motorized suturing devices is that they are mechanically complex and require a large number of rather intricate components. The mechanical complexity of these units increases the likelihood of a malfunction and tends to increase the cost of production.

SUMMARY OF THE INVENTION

The present invention provides a motorized suturing device which is greatly simplified relative to the prior art motorized suturing devices. Consequently, the cost, the time required for assembly and the likelihood of malfunction are all reduced.

The suturing operation requires a needle, and motorized suturing devices typically employ a curved suturing needle. One reason for the complexity of the prior art devices is due to the incompatibility of the motion required by the suturing needle and the motion which is characteristically available from an electric drive motor. More particularly, electric motors provide a rotating output, whereas, the curved suturing needle must oscillate along a path in order to carry out the suturing operation. Some complexity has been introduced as a result of the conversion of the rotating output of the motor to the oscillating movement required by the suturing needle.

This invention converts the rotating motion of the motor to oscillating movement by using only two links which are pivotally connected to each other and to separate shafts, one of which is the drive shaft for the suturing needle. Such an arrangement is also compatible with a small, hand-held suturing device in that these components can be provided in small dimensions. The drive shaft has a longitudinal axis and preferably the oscillatory axis is substantially coincident with the longitudinal axis.

In making a lock stitch, the suturing needle passes through the two layers of flesh which are being sutured together, and on the return stroke, the suturing thread is retained by a loop arm. In order to perform this function, the loop arm must move in a predetermined manner and must be appropriately synchronized to the movements of the suturing needle. Another complexity introduced by the prior art devices is the mechanisms proposed for moving and controlling the loop arm.

This invention simplifies loop arm movement and control by providing for mounting the loop arm for movement along a loop arm path generally transverse to the oscillatory axis of the drive shaft and drivingly coupling the loop arm to the drive shaft. This permits the drive shaft to move the loop arm back and forth along the loop arm path as the drive shaft oscillates. Because both the loop arm and the suturing needle are driven by the drive shaft, the movements of both of these components can be properly phased. For example, the loop arm can be driven by a member, such as an arm or a plate which may couple the loop arm directly to the drive shaft or to some intermediate member.

To permit the suturing needle to be completely withdrawn from the flesh while the loop arm remains on the other side of the flesh layers being sutured, it is necessary that the length of travel of the needle exceed the length of travel of the loop arm. This can be accomplished, for example, by providing appropriate stops for the loop arm and an appropriate connection, such as a lost motion connection.

A preferred mounting construction for the loop arm includes a stationary rod along which the loop arm can reciprocate. If desired, the loop arm can be pivotally joined to a slider mounted on the rod so that the loop arm can pivot about an axis parallel to the oscillatory axis and also translate along the rod. This facilitates pick-up of the thread by the loop arm.

Although the suturing device can be housed in different ways, it is preferred to minimize the size of the head so that it can project into relatively closely confined or inaccessible regions. To accomplish this, the motor and oscillating means are housed separately from the head. To accomplish this, the head includes a head housing section coupled to the oscillating means by an elongated tube. The drive shaft extends through the tube to provide a mechanical driving connection between the oscillating means and the suturing needle and loop arm. The rod for mounting the loop arm can advantageously be mounted on the head housing section, and both the loop arm and the suturing needle are mounted for movement in the head housing section. By removing the oscillating means from the head housing section, the size of the head can be significantly reduced. Also, a bobbin can be advantageously located within the head housing section with the bobbin surrounding the drive shaft.

The invention can best be understood by reference to the following description taken in connection with the accompanying illustrative drawings.

BRIEF DESCRIPTION OF THE DRAWING

FIG. 1 is an elevational view of a suturing device constructed in accordance with the teachings of this invention.

FIG. 2 is an enlarged end elevational view taken generally along line 2—2 of FIG. 1.

FIG. 3 is an enlarged fragmentary sectional view taken generally along line 3—3 of FIG. 2.

FIG. 4 is a sectional view taken generally along line 4—4 of FIG. 3.

FIG. 5 is an enlarged sectional view taken generally along line 5—5 of FIG. 3 with the suturing needle in the initial part of its advancing stroke and just after the drive shaft begins driving the loop arm.

FIG. 6 is an enlarged fragmentary sectional view taken generally along line 6—6 of FIG. 3.

FIG. 7 is a fragmentary sectional view with the suturing needle in the advanced position.

FIG. 8 is a fragmentary isometric view of the forward portion of the suturing device with a portion of the end cap broken away.

FIG. 9 is an enlarged fragmentary sectional view showing the loop arm and how the loop arm is mounted.

FIG. 10 is a view similar to FIG. 5 with the suturing needle in the fully retracted position.

FIG. 11 is a view similar to FIG. 5 with the suturing needle in the fully extended position.

DESCRIPTION OF THE PREFERRED EMBODIMENT

FIG. 1 shows a suturing device 11 which generally includes an electric motor 13, a gear reduction box 15, an oscillator 17, a head 19 and a tube 21 for attaching the head to the oscillator. The motor 13 may be, for example, a 12-volt dc motor which receives electrical current through conductors 23 which lead to a suitable battery or transformer unit (not shown). The circuit to the motor 13 can be manually closed by a switch 24. The circuit remains closed for as long as the switch 24 is depressed but in no event less than the time required for one cycle of operation as described below.

The electric motor 13 provides the usual rotary output, the angular velocity of which is reduced by gears 25 (FIG. 3) of the gear reduction box 15. The gear reduction box 15 may be of conventional construction and, for this reason, is not shown in greater detail herein.

The oscillator 17 includes an oscillator housing or oscillator housing section 27 which comprises a main body 29 and an end cap 31 suitably removably attached to the main body as by a plurality of screws 33 (FIG. 2). The main body 29 is in turn suitably attached to the housing for the gear reduction box 15 which is in turn attached to the motor 15. However, if desired, a single housing could be provided for all of the components of the suturing device 11.

The gear reduction box 15 rotates a first shaft 35 at a relatively slow angular velocity (FIGS. 3 and 4). A collar 37 is mounted on and rotates with the shaft 35 and may be considered as a portion of such shaft. The components within the head 19 are driven by a drive shaft 39 (FIG. 3). In order that rotation of the first shaft can oscillate the drive shaft 39, these two shafts can advantageously be drivingly coupled by a link 41 and an arm 43. The link 41 is pivotally coupled to the collar 37 in spaced relationship to the axis of rotation of the shaft 35 and to the outer end of the arm 43. The arm 43 is keyed or otherwise affixed to the drive shaft 39. Accordingly, rotation of the first shaft 35 causes the drive shaft 39 to oscillate about its own longitudinal axis.

The head 19 includes a head housing section which, in the embodiment illustrated, includes a main body 45, an end ring 47, and an end cap 49 (FIG. 3), all of which are preferably constructed of a suitable rigid plastic material. The main body 45 has an axially extending peripheral flange 51 (FIGS. 3 and 5) which extends axially beyond an end face 53 (FIGS. 3 and 10) of the main body. The flange 51 extends for approximately 270 degrees as shown in FIG. 5. The main body 45 also has an axial cylindrical passage 55 which extends completely through the main body.

A bobbin 57 containing suturing thread 59 surrounds a central protrusion 61 of the main body 45 and is surrounded by an annular flange 63 formed integrally with the main body. The bobbin 57 is retained in position by the end ring 47 which is mounted on the central protrusion 61 and suitably releasably retained by a friction fit or fasteners. As shown in FIG. 1, the suturing thread 59 from the bobbin 57 passes out through an aperture in the flange 63 and through an aperture 64 (FIG. 5) in the flange 51.

The end cap 49 includes an end wall 65 (FIG. 3) and a peripheral wall 67 (FIGS. 2, 3 and 5). A section of the end wall 65 and the peripheral wall 67 has been cut away to form an opening 69 so as to expose portions of the interior of the head 19. The end cap 49 is suitably releasably retained on the main body 45 as by detents (not shown) or a friction fit and can be removed from the main body.

One end of the tube 21 is fixedly mounted within the end cap 31, and the other end of the tube 21 is received within the passage 55 of the main body 45 and suitably frictionally retained therein as by keys 71 (FIG. 6) which cooperate with mating grooves formed in the main body. The drive shaft 39 projects completely through the tube 21 and has a flat-sided lug 73 (FIG. 3) which projects beyond one end of the tube 21.

A suturing needle 75 (FIGS. 3, 5 and 8) is coupled to the drive shaft 39 by a coupling 76 which includes a tubular section 77 (FIG. 3) and a radial arm 79 (FIG. 5). The tubular section 77 is rotatably received within the passage 55 of the main body 45 and has a flat-sided recess for receiving and cooperating with the lug 73 to permit the drive shaft 39 to oscillate the coupling 76. The arm 79 may be integral with the tubular section 77 and extends radially outwardly of the tubular section in close proximity to the end face 53. One end of the needle 75 is suitably fixed to the outer end of the arm 79.

The needle 75 is curved and lies in close proximity to the flange 51. The needle 75 and the flange 51 are preferably concentric. The needle 75 has a sharp point 81 at the end thereof remote from the arm 79 and an eye 83 through which the suturing thread 59 can pass. The thread 59 is guided to the eye 83 by a groove 85 (FIGS. 5 and 8) in the outer surface of the needle 75.

A loop arm 87 (FIGS. 5, 8 and 9) is mounted for movement along a loop arm path by a rod 89, the opposite ends of which are affixed to the flange 51. The rod 89 is preferably linear. Although various mounting arrangements are possible, in the embodiment illustrated, the loop arm 87 includes a slide 91 which slides along the rod 89 and a segment 93 which is pivotally attached to the slide 91 by a pin 94 for pivotal movement about an axis parallel to the axis of oscillation of the drive shaft 39. The segment 93 has a groove 95 forming a foot or tab 97 at the bottom of the loop arm.

The oscillating motion of the drive shaft 39 is used to reciprocate the loop arm 87 along the rod 89. In the embodiment illustrated, this is accomplished by a coupling 99 which, in the embodiment illustrated, is in the form of a plate attached to the arm 79 by a screw 101 (FIGS. 5 and 8) and retained against angular displacement relative to the arm by shoulders 103 which are spaced apart to receive a raised portion 105 of the arm 79. The coupling 99 has an aperture 107 which receives the pin 94 of the loop arm 87. The aperture 107 is oversized in relation to the pin 94 to provide a lost-motion connection.

In the embodiment illustrated, stops 111 and 113 (FIGS. 5, 10 and 11) in the form of shoulders are formed in a recessed region 115 (FIGS. 8 and 10) of the end face 53 of the main body 45. The lost-motion connection provided by the pin 94 and the oversized aperture 107 permits the needle 75 to travel over a larger path than the loop arm 87 even though these elements are mechanically tied together by the coupling 99.

In operation, when the switch 24 is depressed, response to the rotary input of the motor 13 oscillates the drive shaft 39, and the drive shaft 39 oscillates the needle 75 via the coupling 76. Simultaneously, the drive shaft 39 reciprocates the loop arm 87 by means of the coupling 99. These motions are appropriately timed so that a conventional lock stitch can be obtained. The sequencing of the suturing needle 75 and the loop arm 87 is shown by way of example in FIGS. 5, 10 and 11. Initially, the needle 75 is in the retracted position of FIG. 10 with the loop arm 87 engaging the stop 113 and with the needle retracted beyond the loop arm. The initial increment of rotation of the drive shaft 39 moves the needle 75 clockwise from the position of FIG. 10 toward the position of FIG. 5. During this time, the loop arm 87 does not move because the aperture 107 in the coupling 99 prevents the coupling 99 from driving the loop arm. Once the drive shaft 39 has rotated the aperture 107 across the pin 94, the loop arm and needle 75 are both driven clockwise as shown in FIG. 5. This allows the needle 75 to travel beyond the loop arm 87 before the loop arm 87 begins its movement. By varying the length of the aperture 107, the length of travel of the needle 75 when the loop arm 87 is stationary can be adjusted. The return motion is carried out in the same manner in that the aperture 107 initially prevents the coupling 99 from driving the loop arm 87 so that the needle 75 travels a predetermined distance before loop arm movement commences.

When used for suturing, the motion of the needle in traveling from the position of FIG. 10 to the position of FIG. 11 forces the suturing thread 59 through the skin. As the return stroke begins, the loop arm 87, and in particular, the tab 97 thereof retains the thread forced through the skin by the needle so that a loop of thread is retained on the opposite side of the skin from which the needle entered. The ability of the segment 93 of the loop arm 87 to pivot about the pin 94 facilitates pick-up of the thread by the loop arm. The suturing device 11 is moved along the region to be sutured, and the above-described operation is repeated. When the operation of the needle is then repeated, the needle passes through the loop of thread retained by the loop arm 87, and the loop arm picks up the new segment of thread just presented by the needle 75. This operation provides a conventional lock stitch and is continued until the incision is completely sutured.

Each time the switch 24 is closed, the motor 13 rotates a sufficient number of times to drive the needle 75 through one cycle of oscillation. By holding the switch 24 closed, the motor 13 runs continuously.

Although an exemplary embodiment of the invention has been shown and described, many changes, modifications and substitutions may be made by one having ordinary skill in the art without necessarily departing from the spirit and scope of this invention.

I claim:
1. A suturing device comprising:
    a drive shaft;
    means for oscillating said drive shaft generally about an oscillatory axis;
    a suturing needle;
    means for drivingly coupling said suturing needle to said drive shaft whereby said drive shaft can drive said suturing needle back and forth along a first path;
    a loop arm;
    means for mounting said loop arm for movement along a second path, said second path being generally transverse to said oscillatory axis and at least portions of said paths being adjacent;
    means for drivingly coupling said loop arm to said drive shaft to permit the drive shaft to move said loop arm back and forth along said second path; and
    said loop arm mounting means including a rod extending generally transverse to said oscillatory axis and means for mounting the loop arm on said rod for movement in both directions along the rod.

2. A suturing device as defined in claim 1 wherein said means for mounting said loop arm on the rod includes means for mounting said loop arm for pivotal movement about a pivot axis.

3. A suturing device as defined in claim 1 wherein both of said means for drivingly coupling are constructed and arranged so that the length of travel of said needle in moving through one full stroke along said first path is greater than the length of travel of said loop arm in moving through one full stroke along said second path.

4. A suturing device as defined in claim 1 wherein said oscillating means includes an electric motor for providing a rotating output and means responsive to the rotating output for oscillating said drive shaft, said drive shaft having a longitudinal axis which is substantially coincident with said oscillatory axis.

5. A suturing device comprising:
    an electric motor for providing a rotating output;
    a drive shaft;
    oscillator means between the electric motor and the drive shaft and responsive to the rotating output of the motor to oscillate the drive shaft;
    a head housing section;
    said drive shaft extending between said oscillator means and said head housing section and being received at least partially within said head housing section;
    a suturing needle mounted on said drive shaft for oscillatory movement in said head housing section with said drive shaft;
    a loop arm;
    means for mounting the loop arm on the head housing section for movement relative to said head housing section; and
    means coupled to said drive shaft for drivingly coupling said loop arm to said drive shaft to permit the drive shaft to move the loop arm cooperatively with said suturing needle.

6. A suturing device as defined in claim 5 wherein said coupling means includes means for permitting said drive shaft to drive said suturing needle without driving the loop arm during a portion of the time that the drive shaft is oscillating.

7. A suturing device as defined in claim 5 wherein said suturing needle has an elongated groove for guiding suturing thread used by the suturing needle.

8. A suturing device comprising:
    a first shaft mounted for rotation;
    a motor for rotating said first shaft;
    a drive shaft;
    means for mounting the drive shaft for angular movement about an axis;
    a link pivotally coupled to said first shaft;
    an arm coupled to said drive shaft, said link and said arm being pivotally connected to each other so that rotation of the first shaft oscillates said drive shaft about said axis;
    a suturing needle;

means for drivingly coupling said suturing needle to said drive shaft whereby said drive shaft can drive said suturing needle back and forth along a first path;

9. A suturing device comprising:
a drive shaft;
means for oscillating said drive shaft generally about an oscillatory axis;
a suturing needle;
means for drivingly coupling said suturing needle to said drive shaft whereby said drive shaft can drive said suturing needle back and forth along a first path;
a loop arm;
means for mounting said loop arm for movement along a second path, said second path being generally transverse to said oscillatory axis and at least portions of said paths being adjacent;
means coupled to said drive shaft for drivingly coupling said loop arm to said drive shaft to permit the drive shaft to move said loop arm back and forth along said second path; and
said oscillating means including a first shaft, a motor for rotating said first shaft, a link pivotally coupled to said first shaft, and an arm coupled to said drive shaft, said link and arm being pivotally connected so that rotation of said first shaft oscillates said drive shaft.

10. A suturing device comprising:
a drive shaft;
means for oscillating said drive shaft generally about an oscillatory axis;
a suturing needle;
means for drivingly coupling said suturing needle to said drive shaft whereby said drive shaft can drive said suturing needle back and forth along a first path;
a loop arm;
means for mounting said loop arm for movement along a second path, said second path being generally transverse to said oscillatory axis and at least portions of said paths being adjacent;
means for drivingly coupling said loop arm to said drive shaft to permit the drive shaft to move said loop arm back and forth along said second path;
a head housing section, at least one end of said drive shaft being received in said head housing section, said suturing needle being drivingly coupled to said drive shaft adjacent said one end of the drive shaft, and said loop arm mounting means mounting the loop arm on said head housing section for movement along said second path relative to said head housing section; and
a bobbin within said head housing section and surrounding said drive shaft.

11. A suturing device comprising:
a drive shaft;
means for oscillating said drive shaft generally about an oscillatory axis;
a suturing needle;
means for drivingly coupling said suturing needle to said drive shaft whereby said drive shaft can drive said suturing needle back and forth along a first path;
a loop arm;
means for mounting said loop arm for movement along a second path, said second path being generally transverse to said oscillatory axis and at least portions of said paths being adjacent;
means for drivingly coupling said loop arm to said drive shaft to permit the drive shaft to move said loop arm back and forth along said second path;
a head housing section, at least one end of said drive shaft being received in said head housing section, said suturing needle being drivingly coupled to said drive shaft adjacent said one end of the drive shaft, and said loop arm mounting means mounting the loop arm on said head housing section for movement along said second path relative to said head housing section; and
a housing section for said oscillating means and a tube for mounting said head housing section on said housing section for said oscillating means, said drive shaft extending through said tube.

* * * * *